US000001454H

United States Statutory Invention Registration [19]

[11] Reg. Number: H1454

[43] Published: Jun. 6, 1995

Cucuzza et al.

[54] SANITARY NAPKIN PACKAGE WITH INTEGRAL RELEASE LINER

[75] Inventors: Carl C. Cucuzza, Loganville; John M. Raterman, Lawrenceville, both of Ga.

[73] Assignee: Nordson Corp., Westlake, Ohio

[21] Appl. No.: 149,375

[22] Filed: Nov. 9, 1993

[51] Int. Cl.[6] ..... A61F 13/15; A61F 13/16

[52] U.S. Cl. ..... 604/385.1; 604/389; 604/390

[58] Field of Search ..... 604/385.1–398; 206/438, 440

[56] References Cited

U.S. PATENT DOCUMENTS

| | | | |
|---|---|---|---|
| 4,701,178 | 10/1987 | Glaug et al. . | |
| 4,917,675 | 4/1990 | Taylor et al. | 604/385.1 |
| 5,088,993 | 2/1992 | Gaur | 604/385.1 |
| 5,106,384 | 4/1992 | Polski | 604/389 |
| 5,217,448 | 6/1993 | Glaug et al. . | |

FOREIGN PATENT DOCUMENTS

| | | | |
|---|---|---|---|
| 962865 | 2/1975 | Canada | 604/389 |
| 9309743 | 5/1993 | WIPO | 604/389 |

*Primary Examiner*—David Brown

*Attorney, Agent, or Firm*—Howard M. Cohn; Michael L. Gill; Edmund S. Wasp

[57] ABSTRACT

Apparatus and methods for encasing a sanitary napkin in a pouch which eliminates the need for release paper strips and provides for the disposal of the napkin.

2 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SANITARY NAPKIN PACKAGE WITH INTEGRAL RELEASE LINER

FIELD OF THE INVENTION

This invention relates to the packaging and disposal of products for absorbing body fluids, such as sanitary napkins, panty shields, panty liners and adult incontinence pads which are intended to be worn against the perineal portion of the body and held in place by attachment to the crotch portion of an undergarment worn by a user.

BACKGROUND OF THE INVENTION

Sanitary napkins have traditionally incorporated a central absorbent with a permeable body-facing side and a liquid resistant, undergarment-facing side. These napkins are typically secured to the inside crotch area of an undergarment with one or more pressure-sensitive adhesive strips.

More recently, sanitary napkins having side panels or flaps which laterally extend a short distance from the central absorbent and are intended to be folded about the outer crotch portion of the undergarment. See Glaug et al., U.S. Pat. Nos. 4,701,178 and 5,217,448 which are hereby incorporated in their entirety by reference. The side-protecting flaps of the U.S. Pat. No. 4,701,178 are adhered to a release strip during packaging. These release strips, however, present a significant waste disposal problem, as well as contribute to a more expensive sanitary napkin.

The U.S. Pat. No. 5,217,448 of Glaug et al. also relates to a sanitary napkin with side protecting flaps. This type of sanitary napkin does not employ a release strip, but rather includes release surfaces disposed on the undergarment-facing side of the sanitary napkin so that the adhesive elements on the undergarment-facing side of the napkin can be secured thereto.

Still, a need exists for absorbent products that can be conveniently packaged for selective use and convenient disposal. There is also a need to provide packaging which minimizes disposal problems associated with release paper which normally cover adhesive elements of sanitary napkins.

OBJECTS AND SUMMARY OF THE INVENTION

It is an object of the present invention to provide a sanitary napkin encased in a pouch and method of assembling same which obviates the problems and limitations of the prior art products.

It is a further object of the present invention to provide a sanitary napkin encased in a pouch and method of assembling same which eliminates the need for release paper strips.

Yet another object is to provide a sanitary napkin encased in a pouch and method of assembling same wherein the pouch can be used to dispose of a used napkin.

In accordance with the invention, there is provided a sanitary napkin and a pouch and a method of encasing the sanitary napkin in the pouch. A strip of polyethylene material, which forms the pouch, has a longitudinal release strip extending the length of an inside pouch forming surface of a strip of material. Edge adhesive strips extend along the edge portion of each longitudinally extending side of the inside pouch forming surface. An undergarment facing side of the napkin is secured to the release strip with a centrally located adhesive strip. After the napkin is secured to the pouch forming strip, the strip of material is folded into a pouch encasing the napkin.

According to the invention, the folding of the strip of material having the napkin secured thereto into a pouch encasing the napkin is accomplished in several successive steps. A second portion of the strip of material, extending between a first fold line and a second fold line, is folded about the first fold line to overlie a first end portion of the strip, extending between a first transverse end portion of the strip and the first fold line. Next, a third portion of the strip of material, extending between the second fold line and a third fold line, is folded at the second fold line to overlie the first portion of the strip of material. Then, a fourth portion of strip of material, extending between the third fold line and a second transverse end of the strip, is folded at the third fold line to overlie the second portion of the strip of material and form the pouch with the sanitary napkin encased therein.

BRIEF DESCRIPTION OF THE DRAWINGS

The structure, operation, and advantages of the presently preferred embodiment of the invention will become further apparent upon consideration of the following description taken in conjunction with the accompanying drawings, wherein.

DETAILED DESCRIPTION OF THE INVENTION

Figure 1:
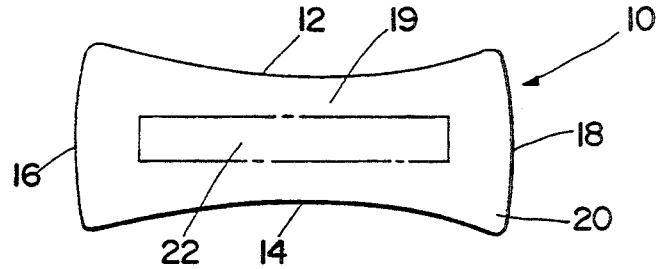
FIG. 1 is a planar view of the undergarment-facing side of a sanitary napkin having traditional styling with an adhesive surface region.

With reference to the drawings, and in particular to FIG. 1, there is shown a preferred sanitary napkin 10 which includes an central absorbent element. Napkin 10 has longitudinally extending sides 12 and 14, transverse ends 16 and 18, a body-facing side 19, and an undergarment-facing side 20. The undergarment-facing side 20 of the central absorbent element includes a centrally located, adhesive surface region 22 which extends longitudinally in the direction of sides 12 and 14 and has sufficient width so that with a coating of adhesive applied thereto, it is adapted to adhere to an undergarment worn by a user.

Figure 2:
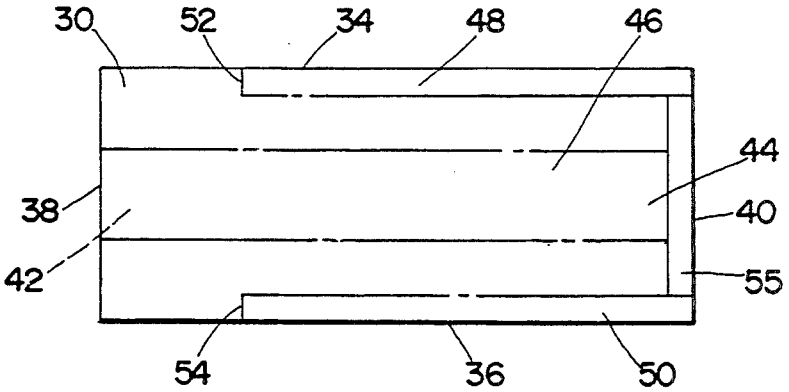
FIG. 2 is a planar view of a strip of material which forms a pouch in which the sanitary napkin is packaged.
Figure 5:
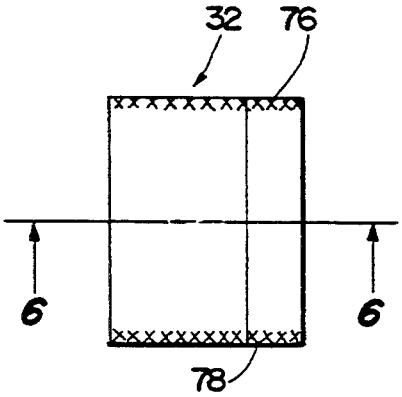
FIG. 5 is a plane view illustrating the sealed lateral edges of the pouch.
Figure 6:
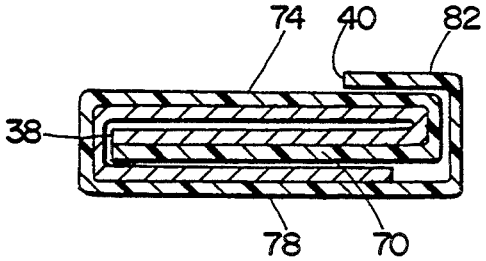
FIG. 6 is a view in cross section, taken along line 6—6 of FIG. 5 of the assembled package, wherein the sanitary napkin and strip of pouch forming material, as illustrated in FIG. 3, are folded into a pouch encasing the napkin.

Referring now to FIG. 2, a strip 30 of material is shown that can be fabricated as a package or pouch 32 to encase and dispose sanitary napkin 10, as shown in FIGS. 5 and 6. The strip 30 has longitudinally extending sides 34 and 36, first and second opposite transverse ends 38 and 40, an exterior facing side 42 which forms the exterior surface of pouch 32, and an interior facing side 44 which forms the interior surface of the pouch. Strip 30 is made of a polymeric material such as polyethylene, polypropylene, or a normally fluid-pervious material which has been treated to be impervious such as a fluid repellent paper. A longitudinally, centrally disposed release surface section 46 extends the length of strip 30 between opposite transverse ends 38 and 40 on interior facing side 44. Longitudinally extending, adhesive edge sections 48 and 50 are also disposed on the interior facing side 44 of strip 30. Sections 48 and 50 extend along the edges of longitudinally extending sides 34 and 36 between transverse end 40 and locations 52 and 54, respectively, which are spaced from transverse end 38. A transverse, adhesive edge section 55 is disposed on interior facing side 44 and extends between sections 48 and 50. The exterior facing side 42 of strip 30 is treated or formed of a suitable material that enables pressure sensitive adhesive, as described herein, to adhere, pull away, and then adhere again, as required.

Figure 3:
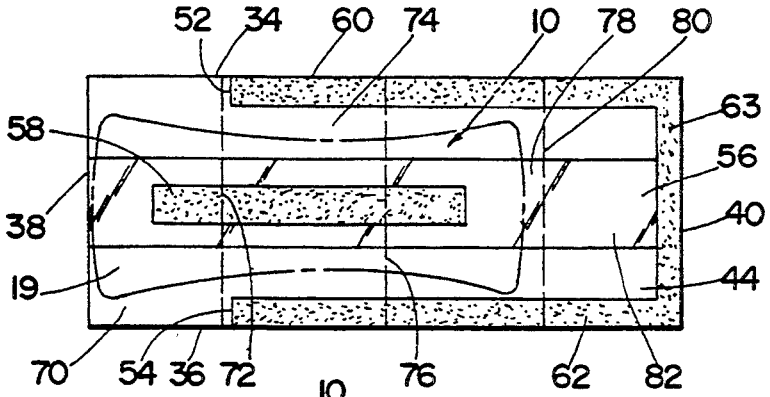
FIG. 3 is a planar view of the strip of material shown in FIG. 2 subsequent to being coated with a release material and an adhesive material to form the inside surface of the pouch into which the sanitary napkin is packaged.

Referring to FIG. 3, there is shown a plan view of the interior facing side 44 of strip 30 subsequent to the fabrication process with sanitary napkin 10 shown oriented in position above interior facing side 44. Initially, the fabrication process proceeds with a release strip 56 being applied, typically by a coating process, directly to release surface section 46. Release strip 56 is then cured by conventional means such as electron-beam radiant energy, ultraviolet energy, or heat. Although a release strip of silicone release material is preferred, any other chemical coating or mechanical treatment known to those of ordinary skill in the art is within the scope of this concept.

The fabrication process continues, as further shown in FIG. 3, with the coating of a central adhesive strip 58, typically of a pressure sensitive, rapid setting, hot melt adhesive material, onto release strip 56. The shape of adhesive strip 58 is substantially identical to centrally located, adhesive surface region 22 on the undergarment-facing side 20 of napkin 10. The adhesive strip 58 is specifically coated onto a release surface so that it can be transferred to the adhesive surface region 22 of napkin 10, as discussed in more detail hereinafter. While a hot melt material is preferred, it is within the scope of the invention to apply any other pressure sensitive adhesive. While the adhesive is shown as being applied in the form of a longitudinally extending strip, it will be understood that various patterns such as spots, squares or transverse lines are suitable.

In addition to the application of central adhesive strip 58, edge adhesive strips 60, 62, and 63 can be coated onto longitudinally extending surface sections 48 and 50 and transverse edge section 55, respectively. Edge adhesive strips 60 and 62 extend along the edges of longitudinally extending sides 34 and 36, respectively, between transverse end 40 and a location 52 and 54, respectively, spaced from transverse end 38. Edge adhesive strip 63 extends along the edge of transverse end 40. Edge adhesive strips 60, 62, and 63 are formed of an adhesive, such as the pressure sensitive, rapid setting, hot melt adhesive material previously described, and are needed to assemble the pouch 32, as described in detail hereinafter. It is also within the terms of the invention for edge adhesive strips 60 and 62 to extend between transverse ends 38 and 40 of strip 30. However, when the combined strip 30 and napkin 10 are aligned and then folded over to form pouch 32, as described in detail below, two layers of pressure sensitive hot melt will overlap each other. When the two layers are pressed together, it is difficult or nearly impossible to open the pouch without destroying strip 30. This is an undesirable result because even after the napkin is removed from the pouch, the latter is designed for reuse to dispose of the napkin.

Figure 4:
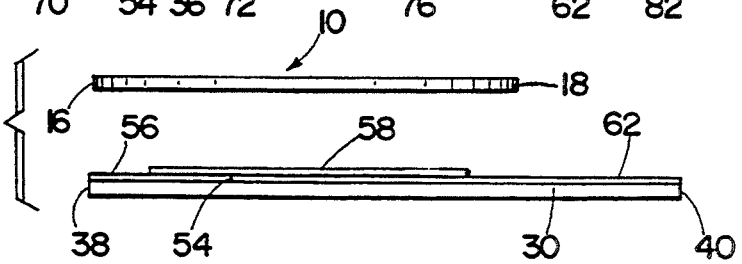
FIG. 4 is side view illustrating the orientation of the sanitary napkin with respect to the strip of pouch forming material during the assembly of the package including the napkin encased in the pouch.

A principle feature of this invention is the packaging of napkin 10 into pouch 32. Strip 30, after being coated with a release strip 56, central adhesive strip 58, and edge adhesive strips 60, 62, and 63 is aligned with respect to napkin 10, as shown in FIGS. 3 and 4, so that center adhesive strip 58 underlies centrally located, adhesive surface region 22. Note that the longitudinally extending sides 12 and 14 of napkin 10 are aligned to overlie the uncoated areas between release strip 56 and edge adhesive strips 60 and 62. The napkin 10 and the strip 30 are pressed together (not shown), causing the transfer of adhesive strip 58 to adhesive surface region 22. Although adhesive strip 58 was lightly held to the polyethylene strip 30 by virtue of the silicone on release surface 46, strip 58 now firmly adheres to adhesive surface region 22 which is neither coated with a release material nor an adhesive.

According to the invention, the folding of the strip of material having the napkin secured thereto into a package or pouch 32 encasing the sanitary napkin is accomplished in several successive steps. Referring to FIG. 3, the strip 30 is labeled with fold lines and intermediate portions to understand the steps in forming the pouch. A first portion 70 extends between a first transverse end 38 of strip 30 and a first fold line 72. A second portion 74 of the strip extends between first fold line 74 and a second fold line 76. A third portion 78 extends between second fold line 76 and a third fold line 80. A fourth portion 82 of strip 30 extends between the third fold line 80 and a second transverse end 40 of the strip 30.

Referring now to FIGS. 5 and 6, a folding technique by which the sanitary napkin is encased within pouch 32 will be described. The first portion 70 of strip 30, having the napkin 10 attached thereto, is folded over along a first fold line 72, shown in FIG. 3, so that the edge surfaces on inside pouch forming surface 44 of strip 30, which are free of adhesive coating, overlap and adhere to edge adhesive strips 60 and 62 on surface 44 of second portion 74. Then, the overlapped first and second portions 70 and 74 are folded along second fold line 76 to overlap third portion 78 of strip 30, between second fold lines 76 and third fold line 80, so that the edge adhesive strips 60 and 62 on surface 44 of third portion 78 overlap the edge surfaces of the outside pouch forming surface 42 of first portion 70 which are free of adhesive coating. Finally, the fourth portion 82 of strip 30 between third fold line 80 and second transverse end 40 is folded along third fold line 80 and wrapped around the outside of pouch forming surface 42 of strip 30. When the edges 76 and 78 of pouch 32 are pressed together, the adhesive strips 60, 62 and 63 are sealed to the respective facing surfaces on the outside pouch forming surface 42 and napkin 10 is securely encased within pouch 32. Since the adhesive strips 60, 62 and 63 are pressure sensitive, pouch 32 can be conveniently opened to remove the napkin 10.

The pouch 32 can be saved for later disposal of napkin 10. That is, after napkin 10 is removed from the pouch 32, the pouch can be folded in the same sequence as just described with napkin 10. Then, the pouch can be opened and a used napkin placed on the inside pouch forming surface 44. Pouch 32 is then rolled up and the adhesive of strips 60 and 62 adjacent the end 40 of strip 30 can be pressed against the outside pouch forming surface 42 for the convenient disposal of the used napkin and pouch. To ensure that pouch 32 is secured, strip 63 of adhesive firmly seals the end 40 of the pouch to outside pouch forming surface 42.

While, the illustrated embodiment coats hot melt adhesive directly on the strip 30 so that it is transferred to napkin 10 during the assembly process, it is also within the terms of the invention to apply hot melt directly to sanitary napkin 10.

While the present invention is described in terms of a sealing process using hot melt which can be resealed for disposal purposes, it is also within the terms of the invention to hot seal the edges of the pouch. While hot sealing will effectively seal the pouch, it does not reseal for disposal purposes.

It is apparent that there has been provided in accordance with this invention apparatus and methods for encasing a sanitary napkin in a pouch which eliminates the need for release paper strips. According to the invention, the pouch can also be used to dispose of the napkin.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

We claim:

1. A method of encasing a sanitary napkin in a pouch, comprising the steps of:

curing a longitudinal release strip of a silicone release material on an inside pouch forming surface of a strip of material to extend between first and second transverse ends of said strip of material, said inside surface having an edge portion along opposite longitudinally extending sides thereof;

affixing first and second edge adhesive strips along said edge portion of each longitudinally extending side, respectively, of said inside pouch forming surface and affixing a third edge adhesive strip along an edge portion of said first transverse end of said inside pouch forming surface to intersect with said first and second edge adhesive strips;

applying a longitudinally extending, central adhesive strip of pressure sensitive, hot melt material directly to said release strip on said strip of material;

aligning an undergarment facing side of said napkin having a centrally located adhesive surface region with respect to said release strip whereby said centrally located adhesive surface region overlies said central adhesive strip and said first and second transverse ends and said longitudinally extending sides of said pouch forming surface extend past the side margins of said napkin;

pressing said strip of material and said napkin together to transfer said adhesive strip from said strip of material to said napkin; and folding said strip of material having said napkin secured thereto into a pouch encasing said napkin, said step of folding said strip of material having said napkin secured thereto into a pouch encasing said napkin comprising the steps of:

folding a first portion of said strip of material, extending between said first transverse end of said strip and a first fold line, about said first fold line to overlap a second portion of said strip, extending between said first fold line and a second fold line;

folding the overlapped first and second portions along said second fold line to overlap a third portion of said strip, extending between said second fold line and a third fold line; and folding a fourth portion of said strip of material, extending between said third fold line and said second transverse end of the strip, along said third fold line to overlap said second portion of said strip of material whereby said pouch is formed with said sanitary napkin encased therein.

2. A sanitary napkin and pouch combination, comprising:

a sanitary napkin;

a strip of material having a longitudinal release strip of siliconè release material cured on an inside pouch forming surface thereof and extending between first and second opposite transverse ends of said strip of material, first and second edge adhesive strips each along an edge portion of longitudinally extending sides of said inside pouch forming surface and a third edge adhesive strip along an edge portion at said second transverse end of said inside pouch forming surface, and said first, second, and third edge adhesive strips being coatings of hot melt adhesive material;

an undergarment facing side of said sanitary napkin secured to said release strip on said strip of material with a central adhesive strip of hot melt adhesive material so that said first and second transverse ends and said longitudinally extending sides of said pouch forming strip extend past the side margins of said napkin; and said strip of material having said napkin secured thereto folded into a pouch encasing said napkin, said strip of material including:

a first end portion, extending between said first transverse end of said strip of material and a first fold line, being folding about said first fold line to overlap a second portion of said strip, extending between said first fold line and a second fold line;

said overlapped first and second portions being folding along said second fold line to overlap a third portion of said strip of material, extending between said second fold line and a third fold line; and a fourth portion of said strip of material, extending between said third fold line and said second transverse end of said strip, being folded about said third fold line to overlap said second portion of said strip of material and thereby form said pouch encasing said sanitary napkin.

* * * * *